(12) United States Patent
Endo et al.

(10) Patent No.: US 7,074,595 B2
(45) Date of Patent: Jul. 11, 2006

(54) GENERAL MEANS OF LABELING PROTEIN BY USING WHEAT EMBRYO CELL-FREE PROTEIN SYNTHESIS SYSTEM

(75) Inventors: Yaeta Endo, Matsuyama (JP); Penmetcha Kumar, Tsukuba (JP); Shigemichi Nishikawa, Kusatsu (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 404 days.

(21) Appl. No.: 10/333,417

(22) PCT Filed: Jul. 18, 2001

(86) PCT No.: PCT/JP01/06226

§ 371 (c)(1),
(2), (4) Date: Mar. 17, 2003

(87) PCT Pub. No.: WO02/08443

PCT Pub. Date: Jan. 31, 2002

(65) Prior Publication Data

US 2003/0162245 A1    Aug. 28, 2003

(30) Foreign Application Priority Data

Jul. 21, 2000  (JP) ............................. 2000-220127
Oct. 15, 2000  (JP) ............................. 2000-306119

(51) Int. Cl.
*C12P 21/02* (2006.01)
*C12P 13/12* (2006.01)
*C12N 5/00* (2006.01)
*C12N 9/06* (2006.01)

(52) U.S. Cl. ..................... 435/70.1; 435/113; 435/410; 435/191

(58) Field of Classification Search ............... 435/70.1, 435/113, 410, 191
See application file for complete search history.

(56) References Cited

U.S. PATENT DOCUMENTS 5,593,856 A    1/1997    Chao et al.
6,905,843 B1   6/2005    Endo et al.

FOREIGN PATENT DOCUMENTS

EP    0 645 450 A1    3/1995
EP    1 221 481 A1    7/2002

(Continued)

OTHER PUBLICATIONS

Nakano et al., "An increased rate of cell-free protein synthesis by condensing wheat-germ extract with ultrafiltration membranes," Biosci Biotech Biochem 58(4):631-634, 1994.*

(Continued)

*Primary Examiner*—Robert A. Wax
*Assistant Examiner*—Rosanne Kosson
(74) *Attorney, Agent, or Firm*—Kilyk & Bowersox P.L.L.C.

(57) ABSTRACT

Utilizing a what embryo cell-free protein synthesis system, there are provided a process for the production of selenomethionine-labeled protein, characterized in that, methionine in a wheat embryo extract for a cell-free protein synthesis obtained by a complete removal of endosperm contaminated is changed to selenomethionine and a cell-free protein synthesis is carried out using a reaction solution composition for protein synthesis containing selenomethionine instead of methionine under a batch condition or a dialysis condition and also the said protein produced as such. There are further provided a process for the production of heavy hydrogen-labeled protein using the same means and also the said protein produced as such.

2 Claims, 5 Drawing Sheets

FOREIGN PATENT DOCUMENTS

| | | |
|---|---|---|
| EP | 1221481 | 7/2002 |
| JP | 05236986 | 9/1993 |
| JP | 07203984 | 8/1995 |
| JP | 2000-236896 | 9/2000 |
| WO | WO 01/27260 A1 | 4/2001 |

OTHER PUBLICATIONS

Boles et al., "Selenomethionyl dihydrofolate reductase from *Escherichia coli*," J Biol Chem 31(5):22217-22223, 1992.*

Boles, J. O. et al. "Selenomethionyl dihydrofolate reductas from *Escherichia coli*. Comparative biochemistry and $^{77}$Se nuclear magnetic resonance spectroscopy", J. Biol. Chem., (1992), vol. 267, No. 31, pp. 22217-22223.

Hendrickson, W. A. et al., "Selenomethionyl proteins produced for analysis by multiwavelength anomalous diffraction (MAD) : a vehicle for direct determination of three-dimensional structure", Embo. J., (1990), vol. 9, No. 5, pp. 1665-1672.

Feeny, J. et al., "A novel method of preparing totally α-deuterated amino acids for selective incorporation into proteins. Application to assignment of $^1$H resonances of valine residues in dihydrofolate reductase", FEBS Letters, (1990), vol. 272, No. 1-2, pp. 197-199.

Madin, K. et al., "A highly efficient and robust cell-free protein sysnthesis system prepared from wheat embryos: plants apparently contain a suicide system directed at ribosomes", Proc. Natl. Acad. Sci. USA, Jan., 2000, vol. 97, No. 2, pp. 559-564.

Kigawa, T. et al., "Cell-free production and stable isotope labeling of milligram quantities of proteins", FEBS Letters, (1999), vol. 442, No. 1, pp. 15-19.

Kigawa, T. et al., "Cell-free systhesis and amino acid-selective stable isotope labeling of proteins for NMR analysis", J. Biomol. NMR., (1995), vol. 6, No. 2, pp. 129-134.

Shaw, D. et al., "High expression and steady-state kinetic characterization of methionine site-directed mutants of *Escherichia coli* methionyl- and selenomethionyl-dihydrofolate reductase", Biochim. Biophys. Acta., (1999), vol. 1429, No. 2, pp. 401-410.

Nakano et al., "An Increased Rate of Cell-Free Protein Synthesis by Condensing Wheat-Germ Extract with Ultrafiltration Membranes," *Bioscience, Biotechnology, Biochemistry*, vol. 58, No. 4, pp. 631-634 (1994).

McConnell et al., "Methionine-Selenomethionine Parallels in *E. coli* Polypeptide Chain Initiation and Synthesis," *Proceedings of the Society for Experimental Biology and Medicine*. Society for Experimental Biology and Medicine (New York, N.Y.) United States, vol. 140, No. 2, pp. 438-641, (1972).

Supplementary European Search Report for EP 01 95 1912, dated Jun. 1, 2004.

U.S. Appl. No. 10/110,454, Endo.

Supplementary Partial European Search Report for EP 99 93 3168 dated Jul. 23, 2004.

Gaitero et al., Purification of a Novel Heat-Stable Translational Inhibitor from Rabbit Reticulocyte Lysates, Federation of European Biochemical Societies Letters, vol. 236, No. 2, 1998, p. 479-483.

Mendez et al., "Primary Structure of ω-Hordothionin, a Member of a Novel Family of Thionins from Barley Endosperm, and Its Inhibition of Protein Synthesis in Eukaryotic and Prokaryotic Cell-Free Systems," European Journal of Biochemistry, vol. 239, 1996, p. 67-73.

Supplemental European Search Report for EP 00966474 dated Sep. 20, 2004.

* cited by examiner (B)

(A)

GENERAL MEANS OF LABELING PROTEIN BY USING WHEAT EMBRYO CELL-FREE PROTEIN SYNTHESIS SYSTEM

This application claims the benefit of earlier filed International Application No. PCT/JP01/06226 filed Jul. 18, 2001.

This application claims priority from Japanese Patent Application No. 2000-220127, 2000-306119, which is incorporated herein by reference.

BACKGROUND OF THE INVENTION

1. Field of the Invention

The present invention relates to a labeling means for protein by selenomethionine utilizing a wheat embryo cell-free protein synthesis system and also to a labeling means for protein using heavy hydrogen.

2. Description of the Related Art

As the completion of the genome project is coming near, focus of the research task has been quickly developing from analysis of gene structures to analysis of gene functions. It is presumed that intracellular protein does not function solely but its function comes into effect as a result of interaction with various protein factors, nucleic acids, lower molecular species, cell membrane components, etc. in a cooperative manner and further that a biological function takes place as a total sum of the said interaction. One of the focuses of the research task after the genome project is to analyze the relation between function of various kinds of protein factor complexes and its structure. Fruit obtained therefrom is expected from research of basic biology, etc. including structural biology and biochemistry to clarify the relation between etiology and gene translation product in a medical field as its application and also to provide extremely important findings in developments of pharmaceuticals.

In the structural biological research of protein, there have been used X-ray crystal analysis method, NMR spectroscopy and neutron scattering method. In order to carry out those methods, it is essential to prepare a large quantity of protein which is labeled with heavy atom, isotope and heavy hydrogen, respectively and maintains the activity. In the conventional X-ray crystal analysis method, it is necessary to prepare at least two kinds of crystals, i.e. "crystal of protein of a natural type" and "heavy atom-labeled crystal of protein where is substituted by heavy atom" for the determination of lattice constant. It is often difficult to prepare the latter crystal and, therefore, there are many cases where crystal structure is not clarified in spite of the fact that the crystallization of the former has been successful. With regard to a technique which has been proposed as a solving means therefor and partly utilized, there is a method utilizing selenomethionine where sulfur atom of methionine is substituted with selenium which is a heavy atom. That is a method in which aimed gene is introduced into incubated cells or *Escherichia coli* followed by incubating in a medium containing selenomethionine. This is a genetic technological means for expressing "the protein for which the gene codes" whereby selenomethionine is introduced into the said protein.

On the other hand, it is necessary to substitute hydrogen atom of protein with heavy hydrogen for steric structure analysis of protein by an NMR spectroscopy or a neutron scattering method and locality analysis of $H_2O$ molecule in a molecule. With regard to a method therefor, there has been used a means where aimed gene is introduced into microbes such as *Escherichia coli* and is incubated in a medium containing an amino acid labeled with heavy hydrogen whereupon genetic product is expressed and protein labeled with heavy hydrogen is prepared.

Selenomethionine-containing protein is useful since it is a one-type crystal obtained from the said protein and its structural analysis is possible and that has been proved already. However, there are many disadvantages in the conventionally conducted method for the labeling of protein with selenomethionine. They are (1) methionine is an essential amino acid which participates not only in protein synthesis but also in various metabolisms in cells and, in addition, since selenium itself shows a strong cytotoxicity, it is not possible to substitute all methionine in the medium with selenomethionine whereby incubation in large quantities is necessary for the preparation of selenomethionine-containing protein in a required amount and (2) selenomethionine is expensive and also highly toxic and, therefore, there is a big problem for a method of discarding the medium containing high concentrations of selenomethionine after the incubation.

On the other hand, labeling of protein with heavy hydrogen is an essential condition for steric structure analysis of protein by an NMR spectroscopy or by a neutron scattering method but, until now, an incubation method of microbe as mentioned above has been an only one. In that method, there are many disadvantages which are to be solved that 1) operation is troublesome, 2) labeling efficiency is low and 3) cost is very high because of necessity of large quantities of amino acid labeled with heavy hydrogen and, in addition, there is a serious problem for a method of discarding the medium due to its strong toxicity.

Further, due to the same reason, there has been developed no practical means using genetic engineering means for the preparation of protein containing amino acid which is labeled with carbon 13 ($^{13}C$) or nitrogen 15 ($^{15}N$) to be used in an NMR spectroscopy.

Under such current circumstances, there has been a brisk demand for the means of preparing a labeled protein which has good efficiency, is less expensive and shows little amount to be discarded as liquid in which the desired amino acid in an aimed protein molecule is able to be labeled in a desired manner where the activity of the said protein is still maintained.

SUMMARY OF THE INVENTION

An embodiment of the present invention is a process for the production of selenomethionine-labeled protein, characterized in that, "methionine in a wheat embryo extract for a cell-free protein synthesis obtained by a complete removal of endosperm" is changed to selenomethionine and a cell-free protein synthesis is carried out using a reaction solution composition for protein synthesis containing selenomethionine instead of methionine under a batch condition or a dialysis condition.

Another embodiment of the present invention is a selenomethionine-labeled protein which is prepared in the above-mentioned producing process.

Still another embodiment of the present invention is a process for the production of heavy hydrogen-containing amino acid-labeled protein, characterized in that, "an amino acid of a natural type in a wheat embryo extract for a cell-free protein synthesis obtained by a complete removal of endosperm contaminated" is changed to heavy hydrogen-labeled amino acid and a cell-free protein synthesis is carried out using a reaction solution composition for protein synthesis containing heavy hydrogen-labeled amino acid instead of an amino acid of a natural type under a batch condition or a dialysis condition.

Another embodiment of the present invention is a heavy hydrogen-containing amino acid-labeled protein prepared in the above-mentioned producing process.

DETAILED DESCRIPTION OF THE PREFERRED EMBODIMENTS

Figure 1:
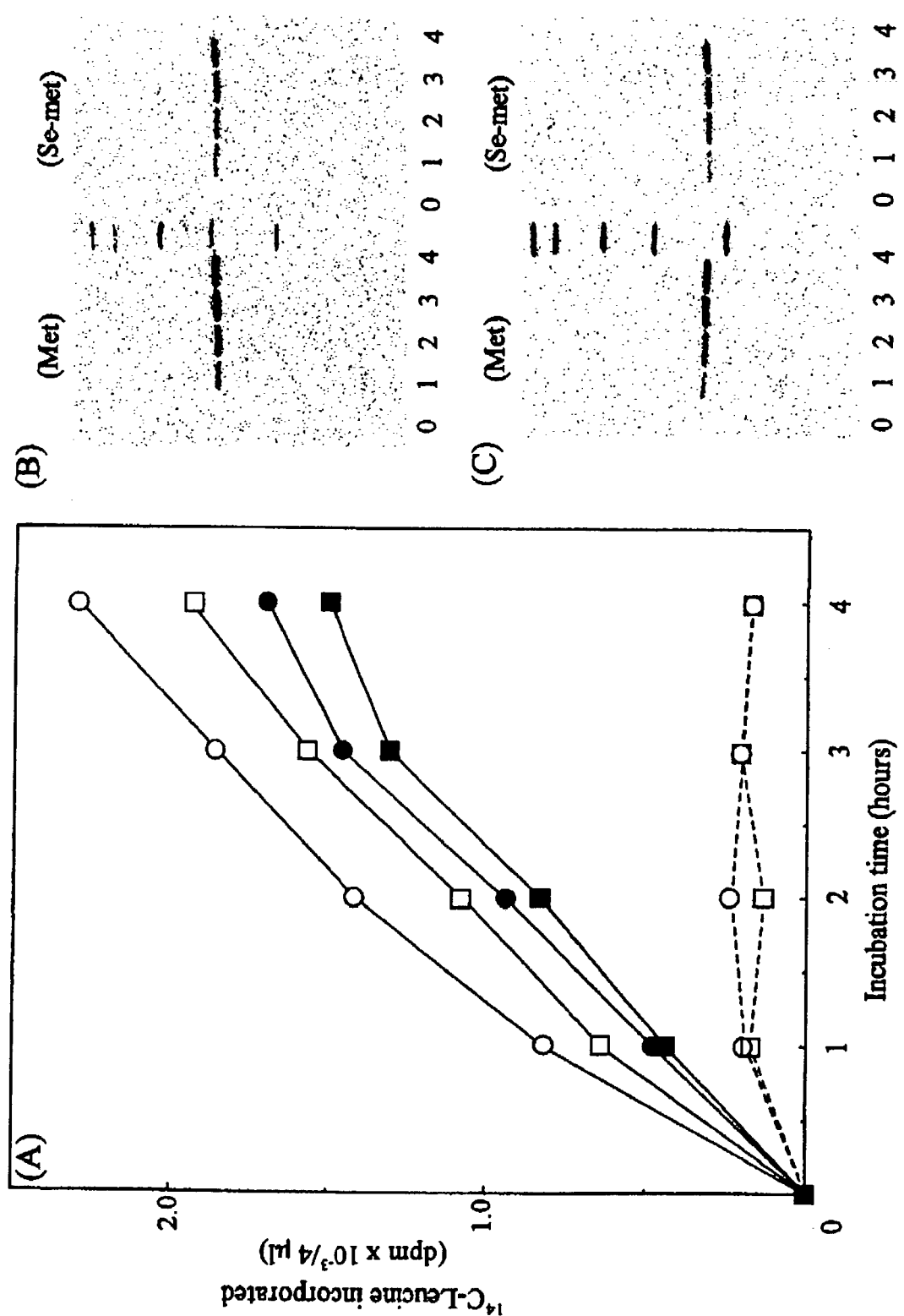
FIG. 1 shows the result where synthesized amount with the lapse of time of "selenomethionine-labeled green fluorescent protein (GFP) and dihydrofolate reductase (DHFR)" by a batch-type cell-free protein synthesis method was checked by means of incorporation (A) of $^{14}$C-leucine into protein and autoradiography [(B) and (C)]. In (A) of FIG. 1, ●—● and ■—■ show synthesized amounts of selenomethionine-containing GFP and selenomethionine-containing DHFR, respectively, in the synthetic reaction system which is carried out using selenomethionine. Synthesized amounts of natural-type GFP and DHFR in the synthetic reaction system using methionine are shown by ○—○ and □—□, respectively. Synthesized amounts of GFP and DHFR in the synthetic reaction systems containing neither methionine nor selenomethionine are shown by ○--○ and □--□, respectively. In (B) and (C) of FIG. 1, Met or Se-met means protein wherein methionine or selenomethionine, respectively, is incorporated.

The process for the production of labeled protein according to the present invention utilizes "a cell-free protein synthetic system". The said producing process has advantages that synthetic efficiency of labeled protein is high and further that highly pure labeled protein can be provided. In addition, due to those advantages, amount of waste liquid is little. Therefore, the process for the production of labeled protein is a very good method as compared with conventional methods.

The cell extract used in "a cell-free protein synthetic system" in the present invention is an extract of wheat embryo or, preferably, a wheat embryo extract wherefrom contamination of endosperm components are substantially completely removed. Wheat embryo extract in the present invention, which is prepared by using wheat embryo solely comprising yellow embryo as starting material that embryo having white small injured parts and embryo having brown and black colors are removed completely, which is able to obtaine by a method shown in Example 1, is particularly preferred.

When protein is labeled with selenomethionine, methionine in wheat embryo extract is substituted with selenomethionine. Method for the substitution will be specifically described in Examples. For example, an extract is firstly prepared from wheat embryo using a mixed solution for extraction containing 20 kinds of amino acids where methionine is previously removed and selenomethionine is added (a solution containing 19 kinds of amino acids and selenomethionine). Alternatively, the extract may be prepared from wheat embryo using a conventional solution for extraction containing all of 20 kinds of amino acids. Then the embryo extract is subjected to gel filtration using a solution containing 20 kinds of amino acids where selenomethionine is added to 19 kinds of amino acids, and a wheat embryo extract containing selenomethionine instead of methionine is prepared.

When protein is labeled with heavy hydrogen, natural type amino acid in the wheat embryo extract is substituted with heavy hydrogen-labeled amino acid. Method for the substitution will be specifically described in the Examples. For example, the natural type amino acid which is to be labeled is previously removed and an extract is prepared from wheat embryo using "a solution for extracting to which the said amino acid which is labeled with heavy hydrogen is added". Or an extract is prepared from wheat embryo using a solution for extracting, which contain 20 kinds of heavy hydrogen-labeled amino acid mixed solution. After that, gel filtration of this wheat embryo extract is carried out using a gel filtration column which is equilibrated with a solution containing the aimed heavy hydrogen-labeled amino acid or 20 kinds of heavy hydrogen-labeled amino acid mixed solution to prepare a wheat embryo extract in which the aimed amino acid among the amino acids in the extract or all 20 kinds of amino acids is/are exchanged with heavy hydrogen-labeled amino acid.

In preparing a selenomethionine-labeled protein, the composition of reaction solution for the synthesis of protein used in the present invention may be that where methionine is substituted with selenomethionine in a composition used for the conventionally known cell-free protein synthetic system (reaction system for cell-free protein synthesis). For example, the said reaction solution is prepared by adding 1,000 units/ml of ribonuclease inhibitor (RNAsin), 30 mM of Hepes-KOH, pH 7.6, 6.95 mM of potassium acetate, 2.65 mM of magnesium acetate, 2.85 mM of dithiothreitol, 0.5 mg/ml of creatine kinase, 1.2 mM of adenosine triphosphate (ATP), 0.25 mM of guanosine triphosphate (GTP), 16 mM of creatine phosphate, 0.380 mM of spermidine, 20 kinds of L-amino acids (each 0.3 mM) containing selenomethionine instead of methionine,0.05% (w/v) of NP-40 etc. to 24% (v/v) solution (concentration: 200$A_{260}$ nm units/ml)by volume of wheat embryo extract.

When heavy hydrogen-labeled protein is to be prepared, there may be used the above composition used in the conventionally known cell-free protein synthetic system in which the natural type amino acid to be labeled is substituted with the said amino acid labeled with heavy hydrogen or all of 20 kinds of amino acids are substituted with the said amino acids labeled with heavy hydrogen.

To this protein synthesis reaction solution is added mRNA coding for the aimed protein to conduct a protein synthesis. Although the mRNA which is prepared by a known method per se can be used, a general-purpose plasmid (pEU) constituted by Endo was used in the present invention in order to synthesize the mRNA which becomes a translation template for protein synthesis (cf. FIG. 4). This plasmid is a plasmid used as a template in a cell-free protein synthesis system which is characterized in being arranged with ① base sequence carrying a promoter function, ② base sequence which becomes transcription template having, in a region corresponding to downstream, at least alfalfa mosaic virus (AMV) leader sequence, omage (Ω) sequence existing in 5'-terminal untranslated sequence (5' UTR) of tobacco mosaic virus (TMV) RNA, base sequence described in SEQ ID NO: 1, 2 or 3 of Sequence Listing, or base sequence having a homology of 70% or more to such sequences and being able to give mRNA having translation initiation activity of about 70% or more as compared with the translation initiation activity of mRNA wherein CAP structure is present, ③ plural cleaved sites by restriction enzyme in a region corresponding to its downstream and ④ 3'-terminal untranslated sequence (3' UTR) comprising at least 500 or more bases in a region corresponding to downstream of termination codon of ORF (Open Reading Frame). The mRNA transcribed from this plasmid has AMV leader sequence, TMVQ sequence, or base sequence described in SEQ ID NO: 1, 2 or 3 mentioned in Sequence Listing at its 5'-terminal untranslated sequence, and also a long 3'-terminal untranslated sequence. Therefore, it is stable and has high translation efficiency. The base sequence described in SEQ ID NO: 1, 2 or 3 mentioned in Sequence Listing is a polynucleotide prepared by designing on the basis of AMV leader sequence and TMVQ sequence to be used as 5'-terminal untranslated sequence.

When this plasmid is used in a cyclic type as it is, "mRNA which is a transcription product" is synthesized as one of various molecular sizes since no special transcription termination site is inserted into the said plasmid. It is also possible that the sequence carrying a terminator function which stipulates the transcription termination site is arranged on upper stream of a promoter region so as to make the molecular size of the transcription product constant. In addition, this plasmid may be subjected to ring opening by cleaving with a restriction enzyme prior to the transcription reaction and used as a plasmid of a straight-chain type.

The mRNA used as a translation template in the present invention may be that which is prepared by using the above-mentioned plasmid or prepared by a known method per se.

With regard to the mRNA which is stable and has a high translation efficiency, it is preferred to use mRNA where the above-mentioned AMV leader sequence, TMVQ sequence or 5'-terminal untranslated sequence (5' UTR) which is possessed by the following virus is arranged in its 5'-terminal side. They are tobacco etch virus (ETV) [Niepel, M. and Gallie, D. D. R. (1999) *J. Virol.*, 73, 9080–9088] [Kawarasaki, Y. et al., (2000) *Biotechnol. Prog.*, 16, 517–521], tobacco vein mottling virus, potato virus and plum pox virus. It is also possible to use internal ribosomal entry site (IRES) existing in the 5'-terminal of the following virus as the above-mentioned 5'-terminal untranslated sequence. They are encephalomyocarditis virus, Theiler's murine encephalomyocarditis virus, foot-and-mouth virus, classical swine fever virus, bovine viral diarrhea virus and hepatitis C virus.

It is also possible to use, for example, untranslated sequence of tomato bushy stunt virus [Wu, B. and White, K. D., (1999) *J. Virol.*, 73, 8982–8988] as untranslated sequence to be arranged at the 3'-terminal for construction of stable mRNA having a high translation efficiency.

It has been also known that an effective translation reaction takes place by an interaction of 5'-terminal untranslated sequence with 3'-terminal untranslated sequence in satellite tobacco necrosis virus [Timmer, R., et al., (1993) *J. Biol. Chem.* 268, 9504–9510] and barley yellow dwarf luteo virus [Guo, L., et al., (2001) *Molecular Cell*, 7, 1103–1109] and those 5'-terminal untranslated sequence and 3'-terminal untranslated sequence may be used for construction of the aimed mRNA.

It is also possible to obtain a sequence having an efficient translation function by means of screening from an RNA pool in random sequence according to a method described in the already-reported papers [Owens, G. C., et al., (2001) *Proc. Natl. Acad. Sci.* 98, 1471–1476] [Venkatesan, A. and Dasgupta, A., (2001) *Mol. Cell. Biol.* 21, 2826–2837] and to utilize the said sequence for the construction of mRNA. It is further possible that the base sequences described in those literatures are utilized as 5'-terminal untranslated sequence or 3'-terminal untranslated sequence of mRNA.

DNA which is used as a template in the construction of mRNA is not limited to cyclic plasmid DNA but a straight-chain double-stranded DNA amplified by PCR may be used as well. In that case, gene of the aimed protein arranged with, "promoter region of T7RNA polymerase as a promoter for the transcription reaction, followed by, 5'-untranslated region of ETV, gene of the aimed protein and, finally, T7RNA polymerase terminator sequence", are transcribed by T7RNA polymerase, whereupon mRNA may be prepared. Follow the preparation of above mRNA, it is then possible to synthesis protein by using a cell-free protein synthetic system.

Synthesis of protein in the present invention is carried out by a cell-free protein synthetic method using the above-prepared wheat embryo extract and protein synthesis reaction solution. The said cell-free protein synthesis may be carried out by a batch system as same as in the conventional method. It is also possible to carry out by a unified cell-free protein synthetic system where dialysis and ultrafilter membrane by which mRNA synthesis (transcription) and protein synthesis (translation) are able to be continuously conducted in the same vessel are utilized using the above-mentioned plasmid into which the aimed gene is inserted. The unified cell-free protein synthetic system and the cell-free protein synthetic method by a batch system will be illustrated as hereunder.

The cell-free protein synthetic method by a batch system means a protein synthesis by one reaction from initiation of the reaction until termination of the said reaction where mRNA obtained by an mRNA synthesis reaction is added to a cell-free protein synthesis reaction system. The mRNA synthesis may be carried out by a method known per se or may be synthesized by utilizing the above-mentioned plasmid. The protein synthesis may be carried out according to a method concerning a cell-free protein synthesis utilizing a wheat embryo extract which was already reported by Endo

[Endo, Y., et al., (1992) *J. Biotech.*, 25, 221–230] [*Proc. Natl. Acad. Sci. USA*, 97, 559–564 (2000)].

On the other hand, in the unified cell-free protein synthetic system of a dialysis type, aimed gene is inserted into the above-mentioned plasmid and this is added to an RNA synthetic reaction solution in its own cyclic form or after being made into straight-chain form to carry out a preliminary reaction at 23~37° C., preferably, at 30° C., for about 5 minutes, preferably, for 10 minutes. Although this preliminary reaction may be omitted if desired, RNA polymerase is bonded to the promoter region of template DNA and the transcription initiation reaction efficiently proceeds during this preliminary reaction stage and, as a result, synthesized amount of protein in the translation reaction stage increases. Accordingly, that is preferably to be carried out. The RNA synthesis reaction solution comprises template DNA, four kinds of substrate ribonucleoside-5'-triphosphates and, if necessary, CAP molecule, RNA polymerase, spermidine, magnesium ion and an appropriate buffer. To be more specific, there may be used, for example, an RNA synthesis reaction solution comprising 80 mM of Hepes-KOH, pH 7.6, 16 mM of magnesium acetate, 2 mM of spermidine, 10 mM of dithiothreitol (DTT), 2.5 mM each of nucleoside-5'-triphosphates [NTP; ATP, GTP, uridine-5'-triphosphate (UTP) and cytidine-5'-triphosphate (CTP)], ribonuclease inhibitor (1,000 units/ml), plasmid DNA (50 µg/ml) and SP6 RNA polymerase (3,000 units/ml). When RNA having a CAP structure at 5'-terminal is synthesized, 5 mM of 7mGpppG is added to the solution.

Then the above RNA synthesis reaction solution containing the above plasmid is mixed with the above protein synthesis reaction solution (for the preparation of selenomethionine-labeled protein, the solution to which selenomethionine is added instead of methionine is used) (for the preparation of heavy hydrogen-labeled protein, the solution containing heavy hydrogen-labeled amino acid instead of natural type amino acid is used). The mixed solution is transferred to a dialysis membrane tube and dipped in a container filled with a previously-prepared outer dialysis-solution (where selenomethionine is added instead of methionine, or, for the preparation of heavy hydrogen-labeled protein, heavy hydrogen-labeled amino acid is added instead of natural type amino acid) for the protein synthesis. When the reaction is carried out at 30° C. for about 3 hours under a stationary condition, mRNA is mainly synthesized at first.

As to the next stage, reaction temperature is lowered to 26° C. and the reaction is continued under a stationary condition together with dialysis. During this process, concentrations of low-molecular substances (particularly ATP and GTP as well as magnesium ion which are set at high concentrations adapting to the optimum concentration for the synthesis of mRNA) in side of the dialysis membrane lower as the dialysis proceeds and becomes near the concentration of "outer liquid for the dialysis" comprising the protein synthesis reaction solution (where selenomethionine is added instead of methionine, or, for the preparation of heavy hydrogen-labeled protein, heavy hydrogen-labeled amino acid instead of natural type amino acid is added) and, in due course, the solution components in the dialysis membrane reaches the optimum concentrations for the protein synthesis reaction.

As a result thereof, the protein synthesis reaction is promoted and its reaction rate becomes the highest whereupon protein is synthesized. This cell-free protein synthesis reaction continues for 60 hours or longer and, when dihydrofolate reductase (DHFR) was synthesized, it was possible to give about 4 mg of protein per ml of the reaction volume.

In this system utilizing a diaysis membrane, any plasmid of a cyclic type and a straight-chain type may be used. However, when synthesis yield and cost are taken into consideration, it is preferred to use plasmid of a cyclic type. Further, this system is able to be carried out under any of the conditions of presence and absence of CAP which promotes the translation initiation activity. However, the CPA per se used for the synthesis of mRNA inhibits a factor necessary for protein synthesis by a strong bonding thereto and, therefore, it is practical to carry out that in the absence of CAP.

It is also possible to carry out labeling of protein with selenomethionine or with heavy hydrogen-containing amino acid in the similar way as above by a cell-free protein synthesis system where the transcription and the translation, by which cell-free protein synthesis is conducted after the synthesis of mRNA in the same container, are unified by utilizing ultrafilter membrane.

Firstly, mRNA is synthesized by a dialysis method using spin column equipped with ultrafilter membrane using the above-mentioned plasmid as a template. The synthetic reaction is carried out at 30~37° C. using the above-mentioned RNA synthesis reaction solution and, although the reaction time is decided depending upon the necessary synthesized amount of RNA, it may be about 3~5 hours in usual cases. With regard to the molecular weight cutting size of the ultrafilter membrane used in the spin column there, although there is no particular limitation so far as it has a pore size which is able to separate "low molecular substances such as substrate for RNA synthesis and by-products upon synthesis" from the synthesized RNA, it is preferably 5,000~100,000. Pore size of such a filter is 10~50 Å.

After completion of the reaction, the spin column which is a reactor is washed by centrifugation whereupon the purified mRNA is collected on the filter. Then the above cell-free protein synthesis reaction solution containing the wheat embryo extract is added to the said spin column and dipped in an outer liquid for dialysis (containing 20 kinds of L-amino acids including selenomethionine in place of methionine or 20 kinds of L-amino acids including heavy hydrogen-labeled amino acid in place of natural type amino acid), a cell-free protein synthesis reaction is initiated at 23° C. and the reaction is carried out under a stationary condition.

Synthetic yield of the protein obtained by that system is in nearly the same degree as in the case of the above system using dialysis membrane. It is also possible to synthesis the protein by a method that mRNA on the filter of the spin column is put "the said filter" into a dialyzing tube by using the above-mentioned system utilizing dialysis membrane. It is further possible in the present invention that mRNA having a CAP structure is also subjected to its efficient protein synthesis reaction after its synthesis and purification in the same manner.

In a system utilizing the ultrafilter membrane, any plasmid of a cyclic type and a straight-chain type may be used and, moreover, this system is able to be carried out under any condition of presence and absence of CAP. Although the synthetic yield of protein is high when mRNA having a CAP structure at 5'-terminal is used, there is no big difference in the synthetic yields for mRNA having a CAP structure at 5'-terminal synthesized from a straight-chain plasmid and mRNA synthesized from a cyclic type plasmid in the absence of CAP and, when the cost is taken into consideration, it is preferred to use a cyclic type plasmid in the absence of CAP.

Both of the above-mentioned two cell-free protein synthesis systems of a unified type are continuous systems where mRNA is firstly synthesized and then protein synthesis is carried out in the same reactor and they are conjugated systems of transcription and translation. In such a system, there may be introduced a means where one or more element(s), selected from mRNA which acts as a translation template for protein synthesis reaction, enzyme for an energy regeneration system, substrates (20 kinds of L-amino acids including selenomethionine in place of methionine or 20 kinds of L-amino acids including heavy hydrogen-labeled amino acid in place of a natural type amino acid) and energy source, is/are added either upon necessity or continuously after initiation of the reaction. They may be added that/those in such a manner that very small amount is added either continuously or intermittently. In addition, in such a system, there may introduced a treatment where a substance necessary for the above-mentioned cell-free protein synthesis reaction is exchanged after initiation of the said synthetic reaction or during the reaction so as to maintain the efficiency of the said synthetic reaction. For example, there may be introduced a means where the desired amount of outer liquid for dialysis comprising a cell-free protein synthesis reaction solution (20 kinds of L-amino acids including selenomethionine in place of methionine or 20 kinds of L-amino acids including heavy hydrogen-labeled amino acid in place of a natural type amino acid) is exchanged continuously or sporadically.

Further, such a system may be equipped with a means where a substance necessary for the above cell-free protein synthesis reaction is stored, so that the said substance is additionally added and exchanged. Furthermore, such a system may be equipped with a discharging means where a by-product at the cell-free protein synthesis reaction is removed from the said synthetic reaction. With regard to the means for addition, storage, exchange and/or discharge of the necessary substance or the by-product, it is possible to select and use one or more means by combining them.

In such a system, when protein coating is previously applied to the surface at least participating in dialysis means or molecular sieve means, for example, the surfaces contacting to the reaction solution in the reactor such as dialysis membrane or ultrafilter membrane, efficiency of protein synthesis is further enhanced. Thus, as a result of a coating treatment using protein, it is possible to increase the efficiency for mRNA transcription and efficiency for the succeeding protein translation. With regard to the protein used for coating, albumin is exemplified but there is no limitation thereto. It is not necessary that protein used for the coating is particularly fixed to the surface participating in the dialysis means or molecular sieve means but just washing with a protein-containing solution for several times will be effective as well. Although that method is simple and preferred, there is no limitation to thereto. For example, in coating the dialysis membrane with albumin, a mixed solution of water and albumin is used as an inner liquid while, as an outer liquid, water is used and dialysis is carried out for several times. Of course, compositions of inner and outer liquids may be reversed. Although there is no particular limitation for the concentration of the solution containing protein for the coating, a saturatedly dissolved concentration is sufficient and lower than that may be acceptable as well.

Incidentally, when the above-mentioned cell-free protein synthesis of unified type or a batch type using wheat embryo extract is carried out in the present invention, it is preferred to conduct the protein synthesis reaction under a stationary condition where the reaction solution is not stirred.

EXAMPLES

Although the present invention will now be illustrated by referring to Examples, the present invention is not limited to the following Examples.

Example 1

Labeling of green fluorescent protein (GFP) and dihydrofolate reductase (DHFR) with selenomethionine was carried out by a cell-free protein synthesis method using wheat embryo extract.

Preparation of wheat embryo extract and cell-free protein synthesis method using the said wheat embryo extract were carried out in accordance with a known method (Endo, Y. et al. (1992) *J. Biotech.*, 25, 221–230) (*Proc. Natl. Acad. Sci. USA* (2000), 97, 559–564).

Firstly, wheat embryo was prepared by an improved method by Johnston, et al. (Johnston, F. B., et al. (1957) *Nature*, 179, 160–161). Firstly, seeds (undisinfected) of chihoku wheat produced in Hokkaido were added to a mill (Rotor Speed Mill pulverisette Type 14 manufactured by Fritsch) at the rate of 100 g per minute and were gently ground at 8,000 rpm. It was ground again at 6,000 rpm and sieved to give a crude embryo fraction (mesh size: 0.71 mm~1.00 mm) and impurities such as seed coat contained in the said embryo fraction were removed by adsorbing with an electrostatically charged substance such as a polyethylene plate.

Then the embryo particles were classified into three fractions—small ones (0.71 mm~0.85 mm), medium ones (0.85 mm~1 mm) and light ones (0.85 mm~1 mm and light as well)—using a sieve and an electrostatically charged substance and, finally, classification by naked eye was conducted to collect yellow embryo. Fraction of the small particles showed the highest protein synthesis activity. The light particles are presumed to be resulted that destruction, in "lightly-injured embryo generated in the embryo during the grinding of the seeds" proceeded during a flotation operation. After that, in order to completely remove wheat edosperm components from the sample comprising yellow embryo prepared as such, the resulted wheat embryo was placed in gauge, and washed with cold distilled water (DDW) with cooling, and then the washed wheat embryo was suspended in a 0.5% (w/v) solution of NP-40 which was a nonionic surface-active agent and repeatedly washed using an ultrasonic wave washing machine until the washing showed no more white turbidity. The wheat embryo was conducted with ultrasonic washing one again in the presence of distilled water and was collected by suction filtration, and then the collected one was washed well with cold distilled water (DDW) to purity the wheat embryo. The wheat embryo purified as such was a product wherefrom endogenous inhibitors for protein synthesis contained in wheat embryo such as trithine, thionine and ribonuclease are substantially removed or, in other words, it was not substantially contaminated with endosperm components.

Preparation of an extract from wheat embryo was carried out in accordance with a conventional method (Erickson, A. H. et al. (1996) *Methods in Enzymol.*, 96, 38–50). The following operations were carried out at 4° C. The above purified wheat embryo was frozen with liquid nitrogen and ground in a mortar and 1 ml of "a solution for extraction which is obtained from partly changed Peterson. et.al's method" (containing 80 mM of Hepes-KOH, pH 7.8, 200 mM of potassium acetate, 2 mM of magnesium acetate, 4 mM of calcium chloride, 8 mM of dithiothreitol, each 0.6 mM of 19 kinds of L-amino acid excluding methionine and each 1 µM of proteinase inhibitors—FUT, E-64 and PMSF) was added per gram of the resulting powder followed by carefully stirring so as not to generate foams. After that, centrifugation was carried out at 30,000 g for 15 minutes and the supernatant liquid thereof was recovered as an embryo extract and subjected to gel filtration using a column of Sephadex G-25 (Coarse) which was previously equilibrated with a solution (containing 40 mM of Hepes-KOH, pH 7.8, 100 mM of potassium acetate, 5 mM of magnesium acetate, 4 mM of dithiothreitol and 20 kinds of amino acids where selenomethionine was supplemented to 19 kinds of L-amino acids excluding methionine). Alternatively, an embryo extract was prepared by the same manner as above using the conventional solution for extraction containing all 20 kinds of amino acids instead of the above-mentioned solution for extraction. In that case, a gel filtration operation was carried out using a column for gel filtration which was previously equilibrated with a solution for gel filtration containing 19 kinds of amino acids excluding methionine and then selenomethionine was supplemented to the resulting wheat embryo extract containing no methionine whereupon a wheat embryo extract was prepared. Concentration of the sample was adjusted to 170~250 $A_{260}$ nm ($A_{260}/A_{280}$=1.5).

With regard to a protein synthesis reaction solution, there was used a solution comprising 24% (v/v) solution by volume of wheat embryo extract (concentration: 200 $A_{260}$ nm units/ml), 1,000 units/ml of ribonuclease inhibitor (RNAsin), 30 mM of Hepes-KOH, pH 7.6, 95 mM of potassium acetate, 2.65 mM of magnesium acetate, 2.85 mM of dithiothreitol, 0.5 mg/ml of creatine kinase, 1.2 mM of ATP, 0.25 mM of GTP, 16 mM of creatine phosphate, 0.380 mM of spermidine, 20 kinds of L-amino acids (0.3 mM each) containing selenomethionine instead of methionine and 0.05% (w/v) of NP-40.

Figure 4:
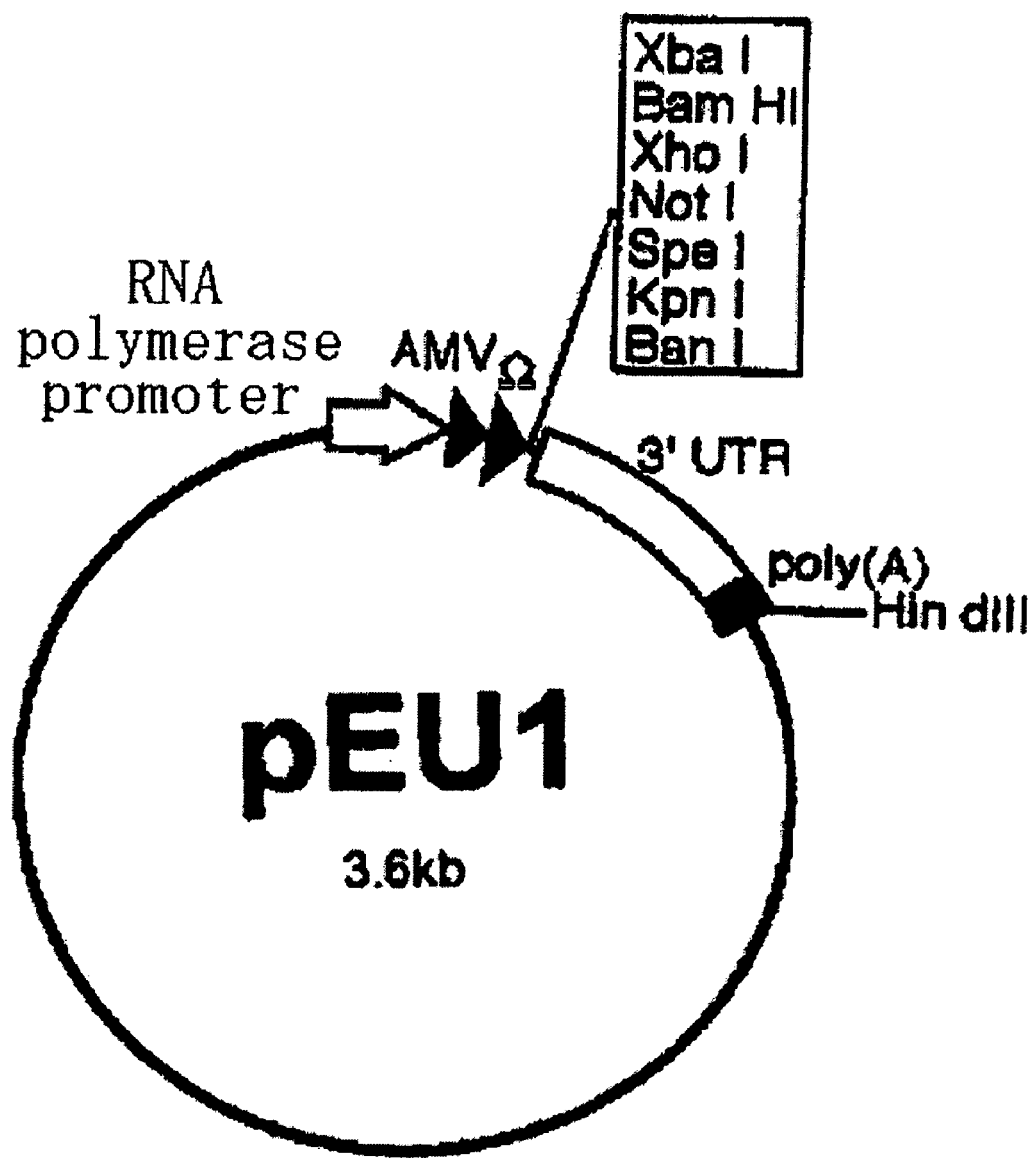
FIG. 4 is a schematic chart showing the constitution of general-purpose template molecule synthesis plasmid (pEU1) for cell-free protein synthesis.

Plasmid for the synthesis of gfp mRNA or dhfr mRNA was prepared in such a manner that, on basis of plasmid pPSP65, base sequence such as "SP6 promoter or T7 promoter" to which RNA polymerase is bonded was inserted into, base sequence to being transcription template of AMV-Ω sequence having an important function in translation initiation reaction of mRNA was inserted into the downstream thereof, then gfp gene or dhfr gene was inserted into further downstream thereof, and a sequence coding for 3' UTR and poly(A) 100 derived from gfp or dhfr gene was inserted into 3'-terminal (FIG. 4). This plasmid was subjected to a ring opening by cleaving a restriction enzyme site (Hind III site) introduced into the downstream of poly(A) sequence with a restriction enzyme Hind III and used as a plasmid DNA of a straight-chain type.

In order to transcribe the mRNA comprising the above plasmid of a straight-chain type, the reactor used was a microspin column (YM-10 manufactured by Amicon) where bottom of the reactor comprised a dialysis filter. mRNA was synthesized by warming an RNA synthesis reaction solution containing the straight-chain plasmid {comprising 80 mM of Hepes-KOH, pH 7.6, 16 mM of magnesium acetate, 2 mM of spermidine, 10 mM of dithiothreitol (DTT), each 2.5 mM of nucleoside-5'-triphosphates [NTP; ATP, GTP, uridine-5'-triphosphate (UTP) and cytidine-5'-triphosphate (CTP)], ribonuclease inhibitor (1,000 units/ml), plasmid DNA (50 µg/ml) and SP6 RNA polymerase (3,000 units/ml)} at 37° C. for 2 hours. Incidentally, YM-10 was used after coating with bovine serum albumin.

After completion of the reaction, the reactor (microspin column) was centrifuged. As a result of centrifugal operation, low-molecular substances such as the substrates (e.g., nucleotide triphosphates and CAP), by-produced pyrophosphoric acid, ion and buffer in the solution were removed from the filter pores while high-molecular substances such as synthesized mRNA remained on the filter. Water was added to the solution, the operation was repeated for several times, low-molecular inhibitors for protein synthesis such as pyrophosphoric acid were completely removed from the synthesized mRNA fraction and the synthesized mRNA was collected on the filter. Incidentally, although the template DNA was not removed by this purifying operation but remained on the filter, it did not show an inhibitory action to the translation reaction.

mRNA was used in the cell-free protein synthesis reaction in such a state that it was recovered as an aqueous solution from the filter where the said mRNA was collected or that it was just collected on the filter.

The mRNA prepared as such was added to the above cell-free protein synthesis reaction solution and protein synthesis was carried out by a cell-free protein synthesis system of a batch type or a unified type. When mRNA recovered as an aqueous solution was used, it was added to the above cell-free protein synthesis reaction solution so as to make it 0.2 µM. Protein synthesis reaction, i.e. a translation reaction, was carried out at 26° C. under a stationary reaction condition.

Amount of synthesized GFP and DHFR in the cell-free protein synthesis method of a batch type was measured by means of incorporation of radioisotope with a trichloroacetic acid-insoluble fraction and the synthesized protein was further analyzed by autoradiography.

Protein which was synthesized in large quantities was detected by an SDS-polyacrylamide gel electrophoresis and by a method staining with Coomassie Brilliant Blue (CBB) [Endo, Y. et al., (1992) *J. Biotech.*, 25, 221–230] [*Proc. Natl. Acad. Sci. USA*, 97, 559–564 (2000)].

Purification of GFP and measurement of its activity by analysis of fluorescence spectrum using a fluorospectrophotometer were carried out in accordance with a method by Deschamps, et al. [Deschamps, J. R. et al., (1995) *Protein Expression and Purification*, 6, 555–558]. In the measurement of fluorescence spectrum, a fluorophotometer of type RF-5000 by Shimadzu was used. DHFR activity was measured by a method of Stanley, et al. [*Methods. Enzymol.* 18, 195–199 (1971)].

The result is shown as follows.

FIG. 1 shows each of the synthesized amounts (A) of GFP and DHFR by a batch system in a protein synthesis reaction system where methionine was substituted with selenomethionine and the result of analysis for each synthesized product by means of autoradiography [(B) and (C)]. (B) in FIG. 1 shows the result for GFP while (C) in FIG. 1 shows the result for DHFR, Met (methionine) in the drawing shows a natural type protein and Set-met (selenomethionine) therein shows a selenomethionine-containing protein. As will be apparent from the autoradiogram, both selenomethionine-containing GFP and selenomethionine-containing DHFR showed the same electrophoretic mobility for the corresponding methionine-containing natural type proteins. In addition, since the bands became dark with the lapse of time, it is noted that their synthesized amounts increased with the lapse of the reaction time. As shown in (A) of FIG. 1, synthesis of selenomethionine-containing GFP (●—●) in the synthesis reaction system where methionine was substituted with selenomethionine showed a reduction in the synthesized amount to an extent of about 20–25% as compared with the synthesis of natural type GFP (○—○) which was a control although selenomethionine-containing GFP was synthesized still efficiently. The similar result was achieved in the case of the synthesis of selenomethionine-containing DHFR (■–■) and the synthesis of natural type DHFR (□–□) which was a control.

On the other hand, in the experiments for the reaction systems containing neither methionine nor selenomethionine, synthetic reaction completely stopped after one hour (○--○). GFP which was synthesized during that period corresponded to about 12% of the amount of selenomethionine-containing GFP which was synthesized by a batch system for 4 hours in the presence of selenomethionine. That shows methionine which was not removed by a gel filtration treatment but remained in the embryo extract was utilized for the synthesis of protein during 1 hour after initiation of the reaction. It further shows that about 12% of GFP amount synthesized by a batch system in the presence of selenomethionine was methionine-containing GFP while 88% thereof was selenomethionine-containing GFP. As will be mentioned later, in a large-scale synthesis in a cell-free protein synthesis system of a dialysis type, ratio of mixed amount of natural type GFP decreases as the selenomethionine-containing GFP synthesis continues and its amount increases and, therefore, it becomes quite little and that can be practically negligible. The same finding was also confirmed in a selenomethionine-containing DHFR synthesis where DHFR gene was used as a template [FIG. 1 (A)] (□--□).

Figure 2:
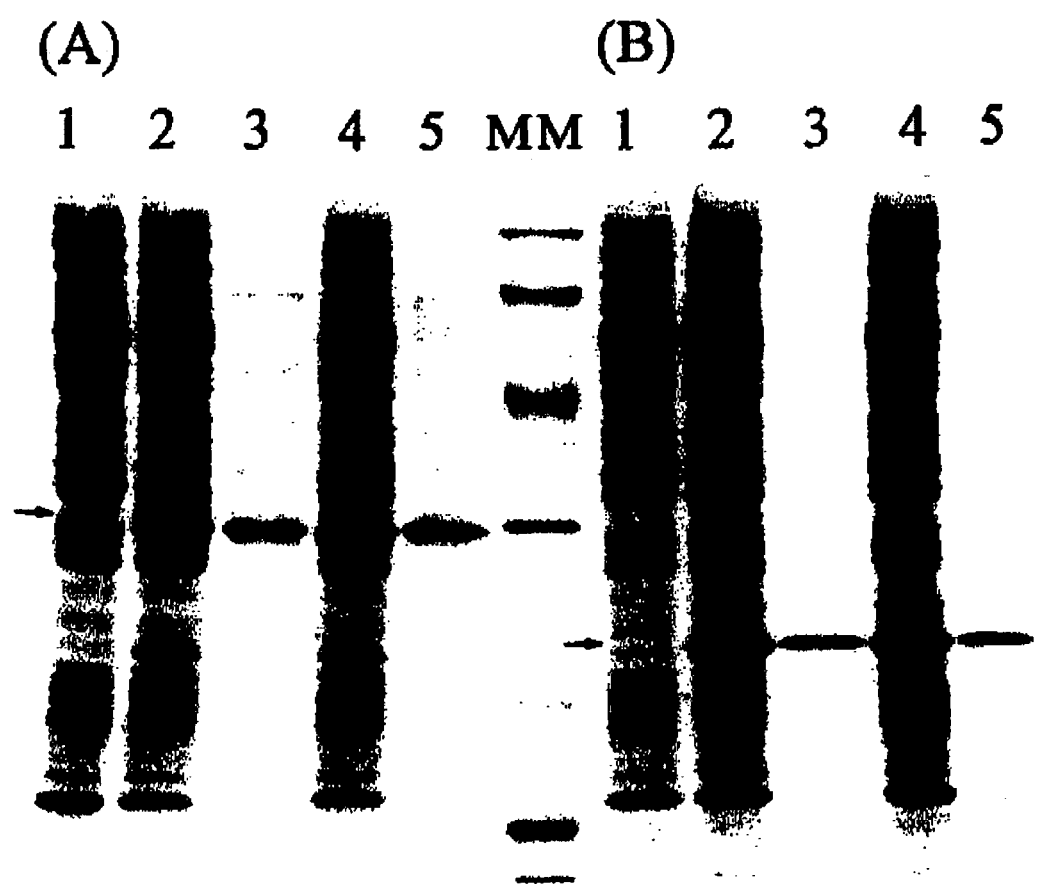
FIG. 2 is an SDS-polyacrylamide gel electropherogram of GFP (A) and DHFR (B) synthesized by a cell-free protein synthetic method of a dialysis type for 48 hours followed by purifying. In both (A) and (B) of FIG. 2, lanes 2 and 3 are the result of electrophoresis for protein of a natural type and lanes 4 and 5 are those for selenomethionine-containing protein. Lanes 2 and 4 are the results of electrophoresis for the solutions themselves after the synthetic reaction and lanes 3 and 5 are those of each protein purified from the said solutions. Lane 1 shows the result where a synthetic reaction is carried out in the absence of protein translation template as a control. In the drawings, an arrow means a band of the produced protein and MM means molecular weight marker

After that, a large-scale synthesis of selenomethionine-containing GFP and selenomethionine-containing DHFR using a unified cell-free protein synthesis method of a dialysis type and proteins were purified from those reaction solutions. FIG. 2 shows SDS-acrylamide gel electrophoretic charts of natural-type (lanes 2 and 3) and selenomethionine-containing (lanes 4 and 5) proteins of each of GFP (A) and DHFR (B) synthesized by this method for 48 hours followed by purifying. An arrow in the drawing shows a band for each protein. It is noted from FIG. 2 that both natural-type and selenomethionine-containing proteins were efficiently synthesized depending on the added template. Lane 1 is an electrophoretic pattern of the reaction solution made to react in the absence of template as a control. In both cases of GFP and DHFR, synthetic efficiency by a unified cell-free protein synthesis method of a dialysis type is high and, therefore, contents of those products in the reaction solution become high whereby it is now possible to easily purify by a conventional method (lanes 3 and 4). In the example of DHFR shown in (B) of FIG. 2, when purification was carried out by affinity chromatography using methotrexate as a ligand, it was possible to prepare a sample where purity of both natural-type and selenomethionine-containing DHFR was nearly 100% by one chromatographic operation (lanes 3 and 4).

Moreover, the experimental result shown by the lanes 3 and 4 shows that selenomethionine-containing DHFR has a strong affinity to methotrexate which is a ligand like natural-type DHFR. That is presumed to mean that the synthesized selenomethionine-containing DHFR has the same enzymatic activity like natural-type DHFR.

More important point is that the content of selenomethionine in the synthesized protein obtained by a unified cell-free protein synthesis method of a dialysis type as above is very high. In other words, the resulting selenomethionine-containing non-natural-type protein is highly pure. Content of selenomethionine can be calculated from the result of selenomethionine content in GFP and DHFR synthesized after 4 hours in the reaction in the presence of selenomethionine shown in FIG. 1 and synthesis kinetics in the absence of methionine and selenomethionine. Amount of the protein synthesized after 4 hours in the batch type reaction was 0.4 mg of GFP and 0.45 mg of DHFR per ml of the reaction solution and, since at least about 80% of methionine residue in those protein were selenomethionine (ratio of methionine-containing protein was about 20% at the largest), amounts of methionine-containing GFP and methionine-containing DHFR were calculated to be 0.08 mg and 0.09 mg, respectively. On the other hand, synthesized amounts after the reaction for 48 hours in the unified cell-free protein synthesis system of a dialysis type were 2.8 mg and 3.1 mg for GFP and DHFR, respectively. Thus, purity of selenomethionine-containing protein which was mass produced in a unified cell-free protein synthesis system of a dialysis type as calculated above was 97.1% for both GFP and DHFR.

As such, introducing rate of selenomethionine into protein by the present invention is far higher as compared with the conventional methods. The conventionally utilized method for introduction of selenomethionine into protein is carried out by a large-scale incubation of *Escherichia coli* and its introducing rate was reported to be 53% at the highest [Huber, R. E. et al., (1967) *Biochim. Bhiophys. Acta*, 141, 587–599]. Accordingly, a process for the introduction of non-natural-type amino acid according to the present invention is very excellent as compared with the conventional methods.

Figure 3:
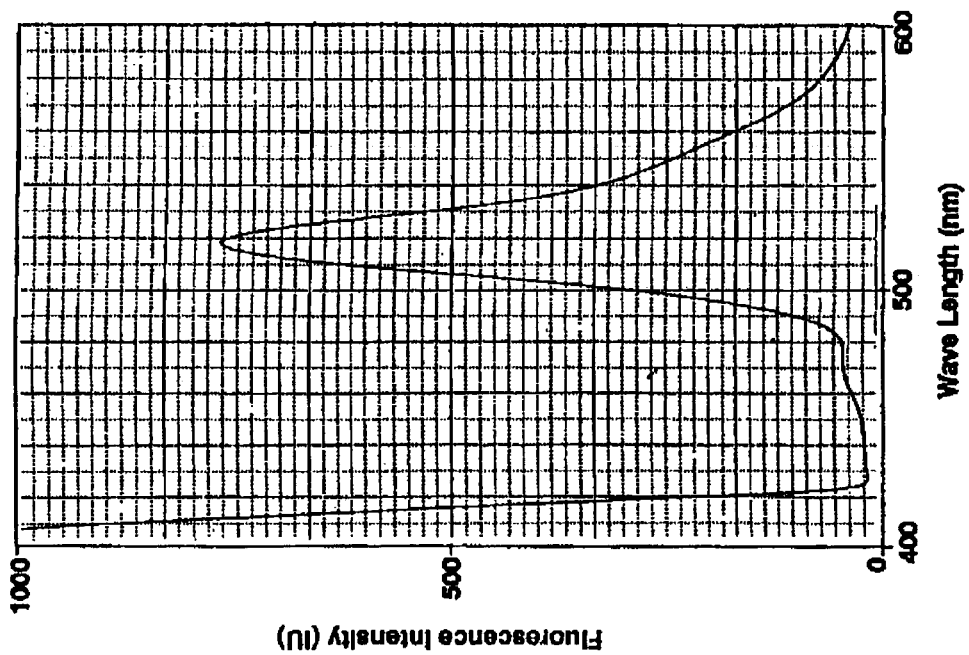
FIG. 3 is a drawing which shows a fluorescence emission spectrum of purified selenomethionine-containing GFP.
Figure 3:
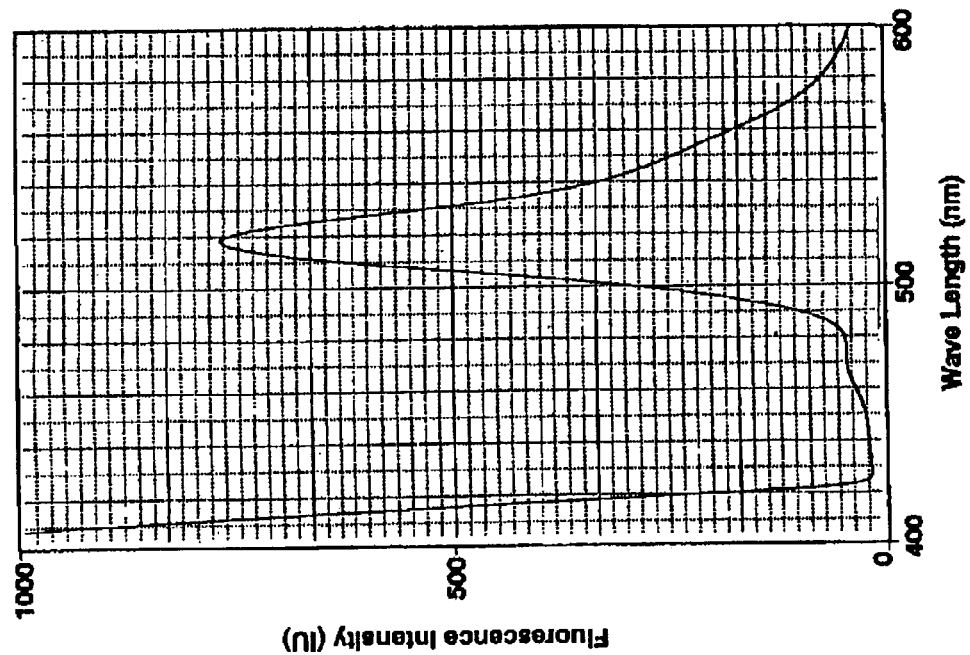

Then enzymatic properties of the selenomethionine-containing proteins purified as such were investigated biochemically. Fluorescence emission spectrum of a certain concentration of the purified GFP preparation shown in FIG. 2 excited at the wavelength of 395 nm was measured within a range of 410 nm to 600 nm and the result is shown in FIG. 3. As will be apparent from FIG. 3, there is no difference between the fluorescence emission spectra of GFP [(A) in FIG. 3] and selenomethionine GFP [(B) in FIG. 3]. Thus, the conclusion is that the change in GFP activity by substituting methionine residue with selenomethionine is not higher than the usual measurement sensitivity.

Result of the investigation of enzymatic properties of DHFR is given in Table 1. As will be apparent from Table 1, there is no different between the enzymes in both the maximum velocity Vmax and Michaelis constant (Km) for nicotinamide adenine dinucleotide phosphate (NADPH) of a reduced type which are parameters for showing enzymochemical properties of natural-type methionine-containing DHFR (Met-DHFR) and selenomethionine-containing DHFR (SeMet-DHFR). Thus, it is apparent that DHFR where methionine residue is substituted with selenomethionine maintains the similar enzymatic activity of the natural-type DHFR.

TABLE 1

|  | Km (μM) | Vmax ($A_{560}$ nm/μg/min) |
|---|---|---|
| Met-DHFR | 11.2 | 0.143 |
| SeMet-DHFR | 10.2 | 0.137 |

After that, mass analysis was carried out with an object of confirming that selenomethionine was incorporated into a site indicated by methionine codon on mRNA during the synthesis of protein or, in other words, selenomethionine was introduced into a site which was originally methionine residue in the protein molecule. From the difference in the mass between the natural-type protein (control) and the selenomethionine-containing protein, it was confirmed that the selenomethionine-containing GFP contained 5.9 selenium atoms and that the selenomethionine-containing DHFR contained 4.8 selenium atoms. Those measured data well agreed with the fact that numbers of methionine residue in GFP and DHFR were 6 and 5, respectively. Further, from the distribution in mass analysis, ratio of unlabeled protein contained as an impurity in those selenomethionine-containing proteins is from about 2% to about 4% and such data well agreed with the above-mentioned calculated data obtained from the experimental data of FIG. 1 and FIG. 2.

Hereinabove, it is shown that, according to the present invention, selenomethionine-containing protein can be synthesized in high efficiency where the activity of the said protein is still maintained. That shows, in the above-mentioned wheat embryo cell-free protein synthesis reaction, any of the factors participating in synthesis of methionyl tRNA, formation of a complex of 40S ribosome subunit with translation initiation aminoacyl tRNA (methionyl tRNA), reaction for elongation of peptide chain and reaction for termination of translation recognizes selenomethionine as same as methionine and the property of incorporating the amino acid analogue into protein is maintained.

Example 2

Labeling of dihydrofolate reductase (DHFR) with heavy hydrogen was carried out utilizing a cell-free protein synthesis system using wheat embryo extract.

With regard to the wheat embryo, that being contaminated with substantially no endosperm component prepared by the method mentioned in Example 1 was used. Preparation of an extract from wheat embryo was carried out by the exactly same method as Example 1 except that the solution for extraction and the solution used for gel filtration contained 20 kinds of heavy hydrogen-labeled L-amino acids instead of 20 kinds of selenomethionine-containing L-amino acids. Concentration of the prepared extract was adjusted to 170~250 $A_{260}$ nm ($A_{260}/A_{280}$=1.5).

Although the composition of the protein synthesis reaction solution is as same as that described in Example 1, it contains 20 kinds of heavy hydrogen-labeled L-amino acids instead of 20 kinds of selenomethionine-containing L-amino acids.

Plasmid for the synthesis of dihydrofolate reductase (DHFR), method for the synthesis of mRNA, method for the synthesis of protein and analysis of the synthesized protein were carried out by the same methods as described in Example 1.

The result is as follows.

Figure 5:
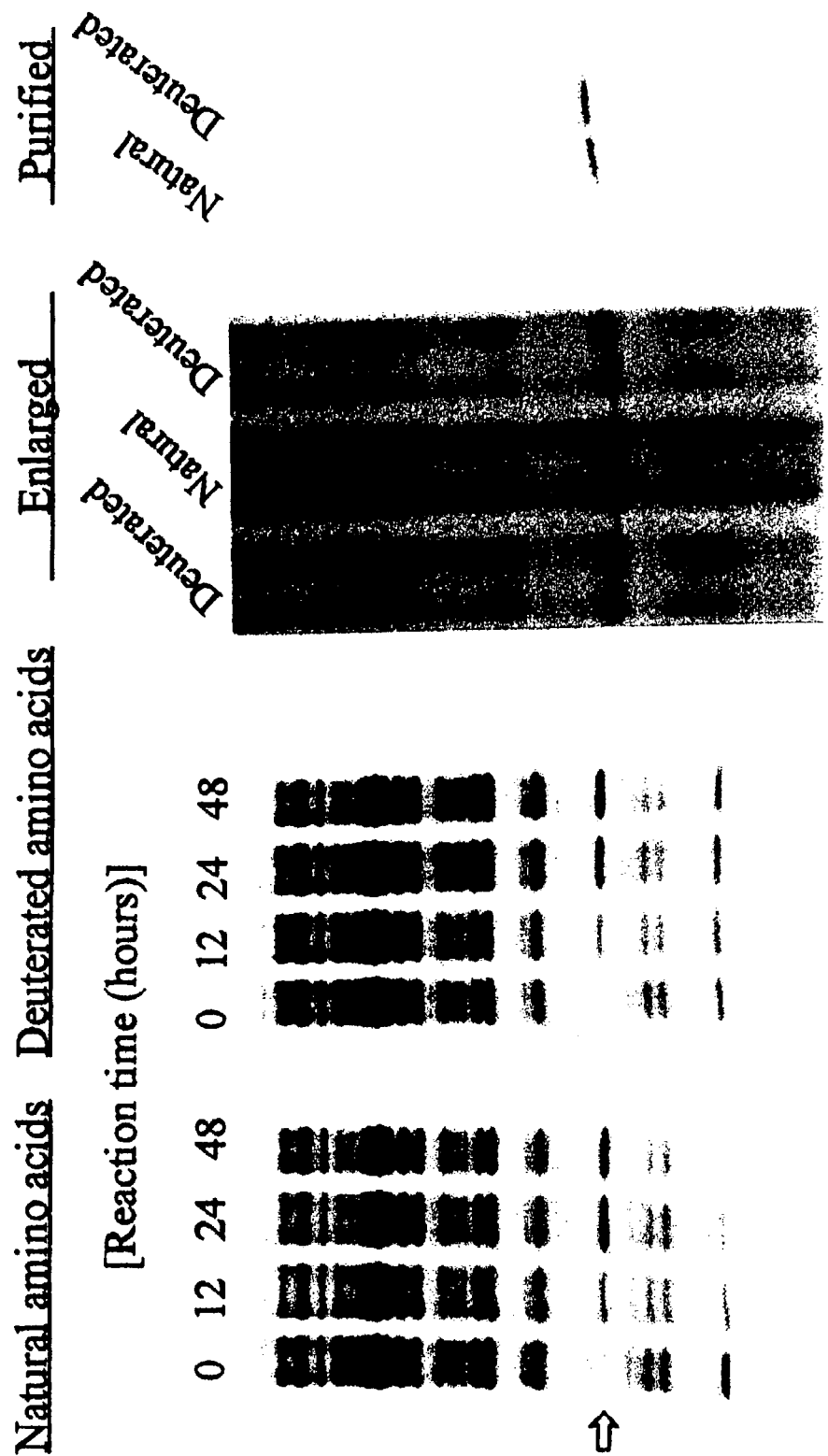
FIG. 5 is electropherogram of heavy hydrogen-labeled DHFR synthesized by a dialytic cell-free protein synthetic method and DHFR purified after synthesis for 48 hours. In the drawings, an arrow shows a band of produced protein and each figure shows reaction time. "Natural amino acids" and "Natural" therein mean the result of synthesis of DHFR using a natural type amino acid and "Deuterated amino acids" and "Deuterated" mean that using heavy hydrogen-labeled L-amino acid. "Enlarged" means an enlarged electrophoretic chart and "Purified" means an electrophoretic chart of purified DHFR.

FIG. 5 shows synthesized amount of DHFR where all of 20 kinds of natural-type L-amino acids were substituted with heavy hydrogen-labeled L-amino acids in the unified cell-free protein synthesis system of a dialysis type. Each 1 μl of the reaction solution was collected after 0, 12, 24 and 48 hours from initiation of the reaction, separated by an SDS-polyacrylamide gel electrophoresis and stained with Coomassie Brilliant Blue (CBB) to detect the protein contained in the said reaction solution. In the drawing, an arrow shows the bands of the produced DHFR. When stained intensity of the bands was measured by a densitometer, it was found that synthesis of DHFR proceeded almost linearly with the lapse of time and that there was no difference between the synthesized amounts of heavy hydrogen-labeled DHFR and of natural-type DHFR. From those facts, it may be concluded that the method of the present invention using wheat embryo cell-free protein synthesis system is an effective method for the synthesis of heavy hydrogen-labeled protein. Yield of the heavy hydrogen-labeled DHFR purified using a methotrexate column after conducting the synthetic reaction for 48 hours was 3.5 mg. It was also confirmed from the enlarged electrophoretic chart (solid line) and migration chart of its purified sample that mobility of heavy hydrogen-labeled DHFR in electrophoresis slightly lowers from that of natural-type DHFR. The phenomenon of lowering in the mobility on an SDS-polyacrylamide gel in the heavy hydrogen-labeled DHFR noted as such is thought to be due to an increase in mass numbers and that directly shows that heavy hydrogen-containing DHFR is synthesized.

Then enzymatic properties of the purified heavy hydrogen-labeled DHFR were biochemically investigated by the same manner as in Example 1. As will be apparent from Table 2, both Vmax and Michaelis constant (Km) to NADPH which are parameters for enzymatic chemical property of natural-type DHFR and heavy hydrogen-labeled DHFR show no difference between both enzymes. Thus, it became clear that DHFR comprising heavy hydrogen-labeled amino acids maintained nearly the same enzymatic activity as the natural-type DHFR.

TABLE 2

|  | Km (μM) | Vmax ($A_{560}$ nm/μg/min) |
| --- | --- | --- |
| Natural-Type DHFR | 13.2 | 0.127 |
| Heavy Hydrogen-Labeled DHFR | 14.7 | 0.261 |

From the above results, it was confirmed that, in accordance with the present invention, protein containing 20 kinds of heavy hydrogen-labeled L-amino acids is able to be synthesized in high efficiency where the activity of the proteins was still maintained.

INDUSTRIAL APPLICABILITY

According to the process for the production of labeled protein according to the present invention, it is now possible to manufacture highly pure labeled protein in high efficiency. Therefore, the process for the production of labeled protein according to the present invention utilizing a cell-free protein synthesis system is useful as a means for preparing the crystal samples for X-ray analysis. In addition, the labeling method described here is similarly useful for the preparation of heavy hydrogen-containing protein as well and, further, according to this method, any desired amino acid is utilized as a general means for labeling the corresponding isotope-labeled amino acid, etc.

More important point is that it is effective for the preparation of protein which is labeled not only with heavy hydrogen but also with isotope such as $^{13}C$ and $^{15}N$ and it is expected to be widely used for structural analysis of proteins.

As such, the process for the production of labeled protein according to the present invention is able to be utilized for the preparation of samples for X-ray crystal analysis of protein, nuclear magnetic resonance analysis and high-order structure analysis by neutron scattering method, etc. or for the clarification of catalytic mechanism of protein utilizing isotope effect.

Free Text of Sequence Listing

SEQ ID NO: 1 —Polynucleotide designed to be used as 5'-untranslated region: gaacaauuac cauacauuuu acauuacaac uaca SEQ ID NO: 2 —Polynucleotide designed to be used as 5'-untranslated region: gaacaacaac aacaacaaac aacaacaaa SEQ ID NO: 3 —Polynucleotide designed to be used as 5'-untranslated region: ggacaacaac aacaa

What is claimed is:

1. A process for the production of selenomethionine-labeled protein, comprising the steps of:
   a) providing a cell-free protein synthesis system comprising a reactor for carrying out protein synthesis by a batch process or a dialysis process, and wherein the cell-free protein synthesis system includes a wheat embryo extract for protein synthesis from which endosperm has been completely removed and in which at least about 80% of the methionine in the wheat embryo extract has been replaced by selenomethionine, and a protein synthesis reaction solution for cell-free protein synthesis in which at least about 80% of the methionine in the protein synthesis reaction solution has been replaced by selenomethionine, and wherein surfaces of the reactor that contact the protein synthesis reaction solution have been subjected to a coating treatment with a coating protein, and
   b) carrying out cell-free protein synthesis with the cell-free protein synthesis system by a batch process or a dialysis process whereby a template mRNA is translated into a selenomethionine-labeled protein.

2. The process for the production of selenomethionine-labeled protein according to claim 1, wherein the protein synthesis reaction is carried out under stationary conditions without stirring.

* * * * *

UNITED STATES PATENT AND TRADEMARK OFFICE
CERTIFICATE OF CORRECTION

PATENT NO. : 7,074,595 B2  Page 1 of 1
APPLICATION NO. : 10/333417
DATED : July 11, 2006
INVENTOR(S) : Endo et al.

It is certified that error appears in the above-identified patent and that said Letters Patent is hereby corrected as shown below:

On the Title Page, Item (30)
IN THE FOREIGN APPLICATION PRIORITY DATA

Change "Oct. 15, 2000" to --October 5, 2000--.

IN THE ABSTRACT; Item (57)

Line 1, change "what" to --wheat--.

Signed and Sealed this

Nineteenth Day of September, 2006

JON W. DUDAS
*Director of the United States Patent and Trademark Office*

UNITED STATES PATENT AND TRADEMARK OFFICE
CERTIFICATE OF CORRECTION

PATENT NO.        : 7,074,595 B2                                      Page 1 of 1
APPLICATION NO. : 10/333417
DATED             : July 11, 2006
INVENTOR(S)       : Endo et al.

It is certified that error appears in the above-identified patent and that said Letters Patent is hereby corrected as shown below:

IN ITEM (73) THE ASSIGNEE SECTION:

Change "CellFree Sciences Co., Ltd., Kanagawa (JP)" to -- CellFree Sciences Co., Ltd., Kanagawa (JP); National Institute of Advanced Industrial Science and Technology, Tokyo (JP); and Wakenyaku Co., Ltd., Kyoto (JP) --.

Signed and Sealed this

Twenty-second Day of May, 2007

JON W. DUDAS
*Director of the United States Patent and Trademark Office*

SEQUENCE LISTING

<160> NUMBER OF SEQ ID NOS: 3

<210> SEQ ID NO 1
<211> LENGTH: 34
<212> TYPE: RNA
<213> ORGANISM: Artificial Sequence
<220> FEATURE:
<223> OTHER INFORMATION: Description of Artificial Sequence:Designed
      polynucleotide used as a 5' untranslated region

<400> SEQUENCE: 1
gaacaauuac cauacauuuu acauuacaac uaca                                    34

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence:Designed
      polynucleotide used as a 5' untranslated region

<400> SEQUENCE: 2
gaacaacaac aacaacaaac aacaacaaa                                          29

<210> SEQ ID NO 3
<211> LENGTH: 15
<212> TYPE: RNA
<213> ORGANISM: Artificial Sequence
<220> FEATURE:
<223> OTHER INFORMATION: Description of Artificial Sequence:Designed
      polynucleotide used as a 5' untranslated region

<400> SEQUENCE: 3
ggacaacaac aacaa                                                         15